United States Patent [19]

Hunter et al.

[11] Patent Number: 5,102,420
[45] Date of Patent: Apr. 7, 1992

[54] SUTURE COATED WITH A POLYETHERAMIDE

[75] Inventors: Alastair W. Hunter, Bridgewater; Henry Pokropinski, Jr., Helmetta, both of N.J.

[73] Assignee: Ethicon, Inc., Somerville, N.J.

[21] Appl. No.: 612,767

[22] Filed: Nov. 14, 1990

[51] Int. Cl.$^5$ .................. A61B 17/00; C08F 283/04; D02G 3/00

[52] U.S. Cl. .................. 606/231; 525/420; 427/2; 428/375

[58] Field of Search .................. 606/228–231; 525/420, 434, 408, 419; 427/2; 428/375

[56] References Cited

U.S. PATENT DOCUMENTS

| | | | |
|---|---|---|---|
| 3,527,650 | 12/1970 | Block | 117/7 |
| 3,942,532 | 3/1976 | Hunter et al. | 128/335.5 |
| 4,043,344 | 8/1977 | Landi et al. | 128/335.5 |
| 4,105,034 | 8/1978 | Shalaby et al. | 128/335.5 |
| 4,361,680 | 11/1982 | Borg et al. | 525/420 |
| 4,578,451 | 3/1986 | Weaver et al. | 528/292 |
| 5,024,792 | 6/1991 | Havens | 264/211 |

OTHER PUBLICATIONS

Flesher, Jr., High Performance Polymers: Their Origin and Development, pp. 401–408, Elsevier Science Publishing Co., Inc., (1986).

*Primary Examiner*—Stephen C. Pellegrino
*Assistant Examiner*—Gary Jackson

[57] ABSTRACT

A surgical suture having a coating thereon of a block poly(ether-co-amide), and a method for improving the knot tiedown performance of a suture by first coating a block poly(ether-co-amide) solution of a block poly(ether-co-amide) onto the surface of the suture and then removing the solvent from the coated suture.

17 Claims, No Drawings

SUTURE COATED WITH A POLYETHERAMIDE

BACKGROUND OF THE INVENTION

This invention relates to coated surgical sutures. More specifically, it relates to sutures coated with a polyetheramide and to a method for improving the knot tiedown performance of a surgical suture.

Surgical sutures often require a surface coating to improve one or more of their performance properties. For example, a multifilament suture typically requires a surface coating to improve the tactile smoothness, pliability and tiedown performance of the suture, so it passes easily and smoothly through tissue during operative procedures. A monofilament suture may also require a surface coating to reduce the stiff feel of the suture and to increase its pliability.

In response to the need for suitable coatings for surgical sutures, numerous patents have disclosed potential coating compositions. U.S. Pat. No. 3,942,532 discloses a polyester coating for multifilament sutures. The preferred polyester coating is polybutilate, which is the condensation product of 1,4-butanediol and adipic acid. U.S. Pat. No. 4,105,034 discloses a multifilament suture coating of a poly(alkylene oxalate), e.g. poly(hexamethylene oxalate). Although the coating compositions disclosed in these patents exhibit excellent handling characteristics and enhance many of the properties of the coated suture, the knot integrity of the coated suture diminishes slightly.

U.S. Pat. No. 3,527,650 discloses a coating composition of polytetrafluoroethylene (PTFE) particles in an acrylic latex. Although PTFE acts as an excellent lubricant to decrease the roughness of multifilament sutures, it has a tendency to flake off during use. Also, this particular coating is a thermoset which requires a curing step for proper application. U.S. Pat. No. 4,043,344 discloses a Pluronics ™ ethylene oxide/propylene oxide copolymer coating for nonabsorbable surgical sutures. Unfortunately, these copolymer coatings lose their lubricity during wet tiedown evaluations.

In view of the deficiencies with the potential candidates for suture coatings, it would be desirable to develop a coating for a suture that can be applied using conventional techniques, that increases the tactile smoothness of the coated suture without sacrificing its physical properties, and that does not adversely affect the knot integrity of the suture.

SUMMARY OF THE INVENTION

In one aspect, the invention is a suture having its surface coated with an amount of a block poly(ether-coamide) effective to improve its knot tiedown performance relative to the knot tiedown performance of the uncoated suture.

In another aspect, the invention is a method of improving the knot tiedown performance of a suture. This method comprises the steps of coating the surface of the suture with an effective amount of a solution of a block poly(ether-co-amide) in an organic solvent, and then removing the solvent from the coated suture.

The block poly(ether-co-amide) coating of this invention can be applied to the surface of a suture using conventional techniques. The knot tiedown performance of the coated suture, which is an indication of its tactile smoothness, dramatically improves without sacrificing the tensile properties of the coated suture. Surprisingly, these improvements in properties are achieved without adversely affecting the knot security of the coated suture.

DETAILED DESCRIPTION OF THE INVENTION

As defined herein, a block poly(ether-co-amide) is a block copolymer with repeating "soft" polyether blocks and "hard" polyamide blocks. The soft polyether blocks enhance the flexibility, hydrophilicity and thermoplasticity of the copolymer and the hard polyamide blocks enchance the physical properties of the copolymer.

The polyether blocks of the copolymer typically contain blocks of polyethylene oxide, polypropylene oxide or polytetramethylene oxide, although other polyether blocks can be envisioned as well. The amount of polyether in the copolymer generally ranges from about 25 to about 80 weight percent, preferably from about 35 to about 75 weight percent. An amount of polyether in the copolymer less than about 25 weight percent may not be suitable for a suture coating because it would lack sufficient lubricity and would be firm or rigid in film coating properties. An amount of polyether in the copolymer greater than about 80 weight percent may result in the preparation of coating copolymers with poor physical properties.

The polyether blocks may not only contain repeating units of polyethylene oxide, for example, but also separate, repeating units of a different polyalkylene oxide such as polypropylene oxide, so long as the total amount of polyether in the copolymer is between about 35 to about 75 weight percent. In a similar fashion, two or more polyalkylene oxides can be copolymerized to form suitable polyether blocks. Preferably, the polyether blocks of the copolymer consist only of repeating units of polytetramethylene oxide.

The polyamide blocks of the block poly(ether-co-amide) can be polyamides such as nylon 6, 66, 611, 612, 10, 11 or 12. The polyamide blocks may contain repeating units of dissimilar polyamides, or copolyamides prepared by reacting at least two different polyamides. Preferably, the polyamide blocks of the copolymer consist only of repeating units of nylon 12.

Block poly(ether-co-amide)s within the scope of this invention are known. In one instance, the polyether bonds, as described in U.S. Pat. No. 4,252,920, U.S. Pat. No. 4,115,475 and U.S. Pat. No. 4,208,493 In another instance, the polyether blocks are terminated with amine groups and linked directly to the polyamide blocks, as described in U.S. Pat. No. 4,808,675. The most preferred block copolymer is PEBAX ™ 3533SA00 block poly(ether-co-amide).

The amount of block poly(ether-co-amide) coated onto the surface of the suture to improve knot tiedown performance will generally depend on the molecular weight of the copolymer and can readily be determined empirically. Surprisingly, the amount of copolymer required to appreciably enhance knot tiedown is typically significantly less than the amount required for conventional coating polymers, e.g. the polybutilate coating described in U.S. Pat. No. 4,105,034. In most instances, the required amount of copolymer decreases as the amount of polyamide in the copolymer increases. Advantageously, the amount of copolymer coated onto the suture ranges from about 0.05 to about 1.0, preferably from about 0.10 to about 0.80 percent of the weight of the coated suture. Generally, amounts greater than 1.0 weight percent may compromise the knot security of the coated suture and amounts below 0.05 weight percent may fail to achieve any significant improvement in suture properties. The suture can be coated with not only one block poly(ether-co-amide), but also a mixture of 2 or more of such copolymers, if desired. Preferably, the suture is coated with one block poly(ether-co-amide).

The block poly(ether-co-amide) coatings of this invention are typically characterized by a weight average molecular weight as determined by gel permeation chromatography ranging from about 45,000 to about 95,000, preferably from about 50,000 to about 90,000.

Sutures within the scope of this invention can be of any type used or contemplated for operative procedures. The suture can be synthetic or natural, absorbable or nonabsorbable, or a monofilament or multifilament in a braided, twisted or covered form. In addition, the sutures can be attached to one or more needles, if desired. Examples of absorbable monofilament sutures include natural sutures such as surgical gut and collagen, and synthetic sutures such as homopolymers and copolymers of p-dioxanone. Examples of absorbable multifilament sutures include sutures prepared from fiber-forming polymers of one or more lactones, e.g. Vicryl® poly(lactide-co-glycolide) multifilament suture. Examples of nonabsorbable monofilament and multifilament sutures include nylon, polypropylene, steel, polyvinylidene fluoride, linen, cotton, silk, and polyesters such as polyethylene terephthalate (PET). The preferred sutures are nonabsorbable, multifilament sutures, preferably polyester sutures. The most preferred suture is PET.

The organic solvent for the block poly(ether-co-amide) coating of this invention is advantageously a solvent or solvent mixture which adequately dissolves the copolymer and has a normal boiling point no greater than 120° C. An example of a suitable organic solvent is a fluorinated aliphatic solvent such as 2,2,2-trifluoroethanol, and an example of a solvent mixture is a mixture of 2,2,2-trifluoroethanol with an aromatic solvent such as toluene. The particular solvent or solvent mixture chosen can be easily determined empirically. Generally, the effectiveness of a particular solvent system depends to a large extent on the ratio of hard to soft blocks in the coating copolymer.

The coating can easily be prepared by simply dissolving the copolymer into the appropriate organic solvent system. The concentration of the copolymer in solution will, of course, depend on the amount of copolymer desirably coated onto the surface of the suture, but generally should range from about 0.2 to about 6.0, preferably from about 0.5 to about 4.0 weight percent.

Once a solution of the block poly(ether-co-amide) is prepared, a suture can be coated using conventional coating techniques, e.g. dipping, spraying, etc. After the coating is applied, the solvent can be removed by drying in air, or by other techniques well known in the art, for example, removing the solvent at an elevated temperature under vacuum.

The organic solvent and the preparation of a coating solution for application is normally required for coating multifilament sutures. However, an alternative approach is feasible for coating monofilament sutures without requiring the preparation of coating solution. If a synthetic monofilament suture is to be coated, then the fiber-forming polymer from which the suture is derived could be coextruded with a suitably low molecular weight block poly(ether-co-amide) so that the block poly(ether-co-amide) could exude to the surface of the fiber during extrusion to increase its tactile smoothness. Such methods have been demonstrated to enhance the lubricity and knotting characteristics of the fiber-forming polymer.

The preferred block copolymer coatings for use in improving tiedown performance of sutures are essentially nonabsorbable. However, a bioabsorbable copolymer especially suited for absorbable sutures can be prepared by first functionalizing a low molecular weight block poly(ether-co-amide), and then copolymerizing it with one or more lactones conventionally used for the preparation of bioabsorbable sutures and suture coatings, e.g. glycolide, lactide, p-dioxanone, trimethylene carbonate, and the like.

The following example illustrates but is in no way intended to limit the scope of the claimed invention. In the example, the tensile properties, tiedown roughness and knot security are each determined using an Instron Tensile Tester. The tensile properties, i.e. the straight and knot tensile strength and the percent elongation, are determined generally according to the procedures described in U.S. Pat. No. 4,838,267. The tiedown roughness is a measure of the knot tiedown performance. It provides an indication of the force required to slide a knot down a suture, and it is determined generally according to the procedure described in U.S. Pat. No. 3,942,532. The knot security, which provides an indication as to the number of throws required to secure a knot so that it fails to slip before cleanly breaking, is measured by first tying a conventional square knot around a mandrel, pulling the knot apart on the Instron Tester to observe whether slipping occurs, and if so, then tying knots with additional throws until 20 out of 20 knots break cleanly without slipping.

EXAMPLE

For each of four runs, a solution of PEBAX ™ block Poly(ether-co-amide) in 2,2,2-trifluoroethanol or 50% w/w trifluoroethanol/toluene is prepared. A size 2/0 (USP standard) Mersilene® PET braided multifilament suture is coated at room temperature with the coating solution using conventional laboratory coating equipment, and the coated suture is subsequently dried in air at elevated temperature to remove the solvent. Table 1 compares the tensile and tiedown roughness properties and the knot security characteristics for each of the four runs with an uncoated Mersilene® PET braided multifilament suture.

TABLE 1
PROPERTIES OF POLYESTER SUTURE COATED WITH BLOCK BLOCK POLY(ETHER-CO-AMIDE)

|  | COATING CONCENTRATION IN SOLVENT, WT. PERCENT | | | | UNCOATED SUTURE CONTROL |
|---|---|---|---|---|---|
|  | 0.5* | 0.5* | 1.0** | 1.0** | |
| PEBAX TM Coating Copolymer | 2533[1] | 3533[2] | 4033[3] | 5533[4] | |
| Percent Solids[4], wt. | 0.1 | 0.1 | 0.1 | 0.1 | — |
| Suture Diameter, mils. | 13.8 | 13.6 | 13.72 | 13.48 | 13.60 |
| Wet[6] Tiedown Roughness, gms. | 130.6 | 108.8 | 158.6 | 184.8 | 350.6 |
| Dry Tiedown Roughness, gms. | 119.8 | 106.5 | 167.8 | 178.3 | 289.4 |
| Wet Knot Security | 4 | 4 | 5 | 5 | 4 |
| Dry Knot Tensile Strength, kpsi | 56.7 | 54.0 | 58.7 | 60.3 | 57.7 |
| Wet Knot Tensile Strength, kpsi | 55.5 | 57.2 | 57.1 | 53.8 | 57.1 |
| Dry Straight Tensile Strength, kpsi | 91.0 | 93.2 | 94.7 | 93.3 | 93.0 |
| Percent Elongation | 15.0 | 17.0 | 16.7 | 12.2 | 16.5 |

*Solvent — trifluoroethanol
**Solvent mixture — 50% w/w trifluoroethanol/toluene
[1]PEBAX TM 2533 is a 62.4/37.6 w/w polytetramethylene oxide/nylon 12 block copolymer with a weight average molecular weight of about 81,000
[2]PEBAX TM 3533 is a 71.6/28.3 w/w polytetramethylene oxide/nylon 12 block copolymer with a molecular weight of about 66,000
[3]PEBAX TM 4033 is a 52.7/47.3 w/w polytetramethylene oxide/nylon 12 block copolymer with a molecular weight of about 60,000
[4]PEBAX TM 5533 is a 37.3/62.7 w/w polytetramethylene oxide/nylon 12 block copolymer with a molecular weight of about 61,000
[5]Determined by measuring the difference in weight between the coated and uncoated suture.
[6]Wet properties are determined after soaking the suture in water at 25° C. for at least 24 hours.

The results indicate that the polyester suture coated with a varying amount of a block poly(ether-co-amide) exhibits significantly improved dry and wet tiedown roughness relative to that of the uncoated suture. The improved roughness is achieved without sacrificing knot security or the tensile properties of the uncoated suture. Generally, a wet tiedown roughness of less than 200 grams for the coated sutures of this invention can be readily obtained.

Similar outstanding results can be obtained with other block poly(ether-co-amide) coatings within the scope of the claimed invention.

We claim:

1. A suture wherein the surface thereof is coated with an amount of a block poly(ether-co-amide) effective to improve the knot tiedown performance of the coated suture relative to the knot tiedown performance of said suture without said coating.

2. The suture of claim 1 wherein the amount of polyether in the block poly(ether-co-amide) is from about 25 to about 80 weight percent.

3. The suture of claim 2 wherein the polyether blocks of the block poly(ether-co-amide) contain repeating units of polytetramethylene oxide.

4. The suture of claim 3 wherein the polyamide blocks of the block poly(ether-co-amide) contain repeating units of nylon 12.

5. The suture of claim 1 wherein the block poly(ether-co-amide) is a copolymer of a low molecular weight block poly(ether-co-amide) and a lactone.

6. The suture of claim 1 wherein the amount of block poly(ether-co-amide) coated onto the surface of the suture ranges between about 0.05 to about 1.0 percent of the weight of the coated suture.

7. The suture of claim 6 wherein the molecular weight of the block poly(ether-co-amide) is between about 45,000 and about 95,000.

8. The suture of claim 7 wherein the suture is a monofilament or multifilament suture with or without one or more needles.

9. The suture of claim 8 wherein the suture is a multifilament suture.

10. The suture of claim 9 wherein the multifilament suture is an nonabsorbable suture.

11. The suture of claim 10 wherein the suture is a polyester.

12. The suture of claim 11 wherein the polyester is polyethylene teraphthalate.

13. A method of improving the knot tiedown performance of a suture comprising the steps of:
    (a) coating the surface of the suture with an effective amount of a solution of a block poly(ether-co-amide) in an organic solvent, and then
    (b) removing the solvent from the coated suture.

14. The method of claim 13 wherein the solution of block poly(ether-co-amide) is a solution of between about 0.2 to about 6.0 weight percent of block poly(ether-co-amide) in 2,2,2-trifluoroethanol or in a mixture of solvents such as 2,2,2-trifluoroethanol and toluene.

15. The method of claim 14 wherein the solvent is removed by drying the coated suture in air.

16. The method of claim 13 wherein the solution of block poly(ether-co-amide) is a solution of between about 0.2 to about 6.0 weight percent of block poly(ether-co-amide) in 2,2,2-trifluoroethanol or in a mixture of 2,2,2-trifluoroethanol and toluene.

17. The method of claim 16 wherein the coated suture is dried at an elevated temperature.

* * * * *